United States Patent [19]

Katz

[11] 4,343,787

[45] Aug. 10, 1982

[54] SHAPED OPHTHALMIC INSERTS FOR TREATING DRY EYE SYNDROME

[75] Inventor: Irving M. Katz, Lansdale, Pa.

[73] Assignee: Merck & Co., Inc., Rahway, N.J.

[21] Appl. No.: 973,975

[22] Filed: Dec. 28, 1978

Related U.S. Application Data

[63] Continuation-in-part of Ser. No. 769,766, Feb. 17, 1977, abandoned, which is a continuation-in-part of Ser. No. 600,168, Jul. 29, 1975, abandoned.

[51] Int. Cl.$^3$ .................... A61K 31/74; A61K 31/79; A61M 31/00; A61M 7/00
[52] U.S. Cl. .................... 424/78; 128/260; 424/80; 424/180
[58] Field of Search ............ 424/78, 80, 180; 128/260

[56] References Cited

U.S. PATENT DOCUMENTS

| | | | |
|---|---|---|---|
| 3,767,788 | 10/1973 | Rankin | 424/78 |
| 3,845,201 | 10/1974 | Haddad | 424/22 |
| 3,856,919 | 12/1974 | Rankin | 424/78 |
| 3,863,633 | 2/1975 | Ryde et al. | 424/78 |
| 3,868,445 | 2/1975 | Ryde et al. | 424/78 |
| 3,875,300 | 4/1975 | Homm et al. | 424/28 |
| 3,911,098 | 10/1975 | Capozza | 424/22 |

OTHER PUBLICATIONS

Maichuk, Invest. Ophthal. 14(2), Feb. 1975–"Ophthal. Drug Inserts".
Lemp et al., Chem. Abst. 76,90019(j) (1972).
Lemp, Intern. Ophthal. Clinic 13(1), pp. 221229 (1973).
Lofholm, "Ophthalmic Products "Handbook of Non--Prescription Drugs", (1973), Pub. Am. Pharm. Assoc. pp. 99–107.
Lemp, Intern. Ophthal. Clinic 13(4), pp. 145-153 (1973).
Laughton, Intern. Opthal. Clinic 13(1), pp. 231–238 (1973).
Dohlman et al., Annals of Opht. 1972, pp. 823-832.

*Primary Examiner*—Douglas W. Robinson
*Attorney, Agent, or Firm*—Edmunde D. Riedl; Mario A. Monaco

[57] ABSTRACT

Water soluble solid ophthalmic inserts for the treatment of dry eye in patients (human and animal), comprising a water soluble solid polymer of appropriate size.

26 Claims, No Drawings

SHAPED OPHTHALMIC INSERTS FOR TREATING DRY EYE SYNDROME

RELATED CASES

This application is a continuation-in-part of U.S. application Ser. No. 769,766 filed Feb. 17, 1977, now abandoned, which application was a continuation-in-part of U.S. application Ser. No. 600,168 filed July 29, 1975, also now abandoned.

BACKGROUND OF THE INVENTION

This invention relates to a water soluble solid ophthalmic insert for the treatment of dry eye syndrome, comprising a water soluble solid polymer insert of appropriate size to readily fit into the cul-de-sac of the eye. It also relates to a method of treating dry eye syndrome patients by applying the solid unmedicated ophthalmic insert into the cul-de-sac; to compositions of said insert, and to a process for preparing these inserts.

The treatment of dry eye syndrome has, in the past, been carried out by the use of ophthalmic preparations which served as wetting agents in the eye to keep the eye moist. These preparations have been of two general types: (1) aqueous solutions or suspensions or (2) ointments.

Historically, these ophthalmic preparations were isotonic aqueous solutions, buffered to the required pH, sterile and contained additives for improved viscosity and longer retention in the eye. However with these solutions, there are problems of dosage, irritation to the eye, stability and most importantly brief duration of effect. In fact, these aqueous solutions are effective for, at the most, a few minutes or so. It was partly because of this very short retention time that ophthalmic solutions were employed using water soluble polymer such as methylcellulose and other related cellulose derivatives as well as polyethylene oxide among others (see for example, U.S. Pat. Nos. 3,767,788, 3,767,789, emp, M.A. Int. Ophthal. Clin. 13 (No. 4) page 145 (1973) and 13 (No. 1) page 221 (1973), "External Eye Problems in the Elderly" by Frederick H. Theodore, M.D. Gereatrics 30: 71–77, April 1975 and Annals. of Ophthalmology by Bach et al, Vol. 4, pages 116–119 (1972) in an attempt to prolong the effectiveness of the preparation in the eye. The use of these polymers added to the viscosity of these ophthalmic solutions thereby affording a longer contact time of the medication with the eye. Nonetheless, these higher viscosity ophthalmic preparations are effective for no more than five to ten minutes and accordingly still require frequent applications to the eye to be effective. A recent application, Ser. No. 553,399 filed Feb. 26, 1975 discloses the use of hydroxypropylcellulose in solid form as a carrier for a medicament, such as pilocarpine, in the treatment of glaucoma. Here the hydroxypropylcellulose is employed as a carrier for the medicament but as in other applications to also afford further contact time of the medication with the eye. However, there is no suggestion therein that the insert does dissolve at a uniform rate or for that matter that it would be effective in the treatment of dry eye, but rather the medicament is leached out of the hydroxypropylcellulose which eventually dissolves.

It is an object of the present invention to provide an ophthalmic insert which serves as an artificial tear material useful for the treatment of dry eye characterized by having a long effective action over a period of at least several hours. This ophthalmic insert, therefore, when inserted in the cul-de-sac of the eye slowly dissolves, affording a continuous long term release of artificial tears and thereby eliminating the need for frequent installation of eye drops or ointments.

It has been surprisingly found that a non-toxic water soluble solid polymer inserted into the cul-de-sac of the eye is effective in relieving the symptoms of dry eye. It was not expected that such a polymer, which in the past had been used merely as a viscosity agent, could in a solid form act by itself to relieve such symptoms. It has also been surprising to find that such a water soluble polymer in solid form could uniformly dissolve in the eye and provide "artificial tear" for a period of at least several hours. This is particularly true of patients with dry eye syndrome since with limited amount of water available in the eye of such a patient, it would not be expected that proper dissolution of the polymer would occur.

DETAILS OF THE INVENTION

This invention relates to a non-toxic solid water soluble polymer ophthalmic insert useful in the treatment of dry eye syndrome. The insert may be placed into the cul-de-sac of the eye to obtain long term release of "artificial tears". The polymer used to form the inserts of this invention may be any water soluble non-toxic polymer. For example, one may employ water soluble polymers of cellulose derivatives such as methylcellulose, alkali carboxyloweralkyl cellulose (sodium carboxymethyl cellulose), hydroxyloweralkyl cellulose, (hydroxmethyl cellulose, hydroxyethyl cellulose, hydroxypropyl cellulose), hydroxyloweralkyl-lower alkyl cellulose, (hydroxypropylmethyl cellulose); (Lower alkyl meaning from 1–4 carbon atoms); natural products (natural gums), such as gelatin, metal alginates (Na, K, Ca, Zn, Al), pectins, tragacanth, karaya, chondrus, agar, acacia; the starch derivatives such as hydroxyethyl starch ethers, hydroxypropyl starch; dextran, lower hydroxyalkyl dextran, carboxy-loweralkyl dextran, polyalkylene glycols (polyethylene and polypropylene glycols), as well as other synthetic derivatives such as poly vinylmethyl ether, poly ethylene oxide, neutralized carbopol and xanthan gum, and mixtures of said polymer.

Preferably the solid insert is prepared from cellulose derivatives such as methylcellulose, sodium carboxymethyl cellulose, hydroxyethyl cellulose, hydroxypropyl cellulose or hydroxpropylmethyl cellulose or from natural gums such as metal aliginates and pectins and expecially the cellulose derivatives. Hydroxypropyl cellulose, one of the preferred polymers for the preparation of these insert of the invention is available in several polymeric forms, all of which are suitable in the preparation of these inserts. Thus the product sold by Hercules, Inc. of Wilmington, Del. under the name KLUCEL such as KLUCEL HF, HWF, MF, GF, JF, LF and EF which are intended for food or pharmaceutical use are particularly useful in preparing the inserts of this invention. The molecular weight of these polymers useful for the purposes described herein may be at least 30,000 to about 1,000,000 or more. Similarly, an ethylene oxide polymer having a molecular weight of up to 5,000,000 or greater, and preferably 100,000 to 5,000,000 can be employed. Further, for example, POLYOX a polymer supplied by Union Carbide Co. may be used having a molecular weight of about 50,000 to 5,000,000 or more and preferably 3,000,000 to 4,000,000.

Other specific polymers which are useful in this invention are hydroxypropylmethyl cellulose having a molecular weight of from about 10,000 to 1,000,000 or more, particularly up to about 200,000 and especially about 80,000 to about 125,000; methyl cellulose having a molecular weight of from about 10,000 to about 1,000,000 or more, preferably up to about 200,000 and especially about 50 to 100,000; CARBOPOL (carboxyvinyl polymer) of B. F. Goodrich and Co. designated as grades 934, 940 and 941, pectin 20 to 400,000, and gelatin; either type A or type B gelatin, having a gel strength ranging from 90 to 300 Bloom and preferably from 200 to 250 Bloom. It is clear that for the purpose of this invention the molecular weight of the polymer is not critical. Water soluble polymers can be used having an average molecular weight which will afford dissolution of the polymer in any desired length of time. The inserts, therefore, can be prepared to allow for retention and accordingly effectiveness in the eye for any desired period.

The insert can be of any desired shape and size which in its outer limits can cover the entire globe of the eye including the cornea and sclera and extend from the inferior, superior, nasal and temporal limits to the conjunctival sac. Accordingly the insert can be in the form of a square, rectangle, oval, circle, doughnut, semicircle, ¼ moon shape, and the like. Preferably the insert is in the form of a rod, doughnut, oval or ¼ moon. The insert can be readily prepared, for example, by dissolving the polymer in a suitable solvent and the solution evaporated to afford a thin film of the polymer which can then be subdivided to prepare inserts of appropriate size. Alternatively the insert can be prepared by warming the polymer and then molded to form a thin film. Preferably, the inserts are prepared by molding or extrusion procedures well known in the art. The molded or extruded product can then be subdivided to afford inserts of suitable size for administration in the eye. In order to properly fit into the cul-de-sac of the eye without excessive irritation, and yet to be effective for its intended use, the insert should have a surface area of from about 5 to about 800 sq. mm. preferably 5-400 and especially 5-100 sq. mm. and most especially 5-50 sq. mm. a length of from about 1-30 mm. preferably about 5-20 mm. and especially 2-15 mm. and a width and height of from about 0.25 mm. to about 30 mm., preferably from about 1-10 mm. and especially 1-5 mm. For example, castings or compression molded films having a thickness of about 0.25 mm. to 15.0 mm. can be subdivided to obtain suitable inserts. Rectangular segments of the cast or compressed film having a thickness between about 0.5 and 1.5 mm. can be cut to afford shapes such as rectangular plates of 4×5-20 mm. or ovals of comparable size. Similarly, extruded rods having a diameter between about 0.5 and 1.5 mm. can be cut into suitable sections to provide the desired amount of polymer. For example, rods of 1.0 to 1.5 mm. in diameter and from about 2-20 mm. long are found to be satisfactory. The inserts may also be directly formed by injection molding. It is preferred that the ophthalmic inserts of the present invention be formed so that they are smooth and do not have any sharp edges or corners which could cause damage to the eye. Since the term smooth and sharp edges or corners are subjective terms, in this application these terms are used to indicate that excessive irritation of the eye will not result from the use of the insert.

The ocular inserts of this invention can also contain plasticizers, buffering agents and preservatives. The invention is therefore also directed to compositions containing these materials along with the water soluble polymer. Plasticizers suitable for this purpose must, of course, also be completely soluble in the lacrimal fluids of the eye. Examples of suitable plasticizers that might be mentioned are water, polyethylene glycol, propylene glycol, glycerine, trimethylol propane, di and tripropylene glycol, hydroxypropyl sucrose and the like. Typically, such plasticizers can be present in the ophthalmic insert in an amount ranging from up to 1 about 40% by weight. A particularly preferred plasticizer is water which is present in amounts of at least about 5% up to about 40%. In actual practice, a water content of from about 5% to about 20% is preferred since it may be easily accomplished and adds the desired softness and pliability to the insert.

When plasticizing the solid product with water, the product is contacted with air having a relative humidity of at least 40% until said product picks up at least about 5% water and becomes softer and more pliable. In a preferred embodiment, the relative humidity of the air is from about 60% to about 99% and the contacting is continued until the water is present in the product in amounts of from about 5% to about 20%.

Suitable water soluble preservatives which may be employed in the insert are sodium bisulfite, sodium thiosulfate, ascorbate, benzalkonium chloride, chlorobutanol, thimerosal, phenylmercuric acetate, phenylmercuric borate, parabens, benzyl alcohol and phenylethanol. These agents may be present in amounts of from 0.001 to 5% by weight of solid insert, and preferably 0.1 to 2%.

Suitable water soluble buffering agents are alkali, alkali earth carbonates, phosphates, bicarbonates, citrates, borates, and the like, such as sodium phosphate, citrate, borate, acetate, bicarbonate and carbonate. These agents may be present in amounts sufficient to obtain a pH of the system of between 5.5 to 8.0 and especially 7-8; usually up to about 2% by weight of polymer.

The water soluble polymer inserts when applied to the eye of a patient having dry eye syndrome with at least one symptom of corneal pathology, photoplobia, burning, foreign body sensations and instantaneous or near instantaneous break up time measurements, significantly improves patient comfort for at least several hours, prolonges the break up time and thickens the pre-corneal tear film for at least several hours compared to little or no improvement with commercially available liquid artificial tears. Accordingly, this invention also provides a method of treating the eye of a patient exhibiting the symptoms of dry eye. The ophthalmic insert may contain any convenient weight of polymers. As a practical matter, too little polymer will lead to dissolution over too short a period of time while too much may make the insert too bulky. Accordingly, it is preferred that the insert contain from about 1 mg. to 1000 mg. of water soluble polymer, more particularly from 2 to 300 mg., and especially from 5 to 100 mg. The time of dissolution of the insert is dependent upon each patients natural supply of tears as well as the particular polymer employed. Usually the time of dissolution is between about 4 hours to 7 days, and preferably 6 to 24 hours, but suitably may be as little as one hour.

This invention also provides a process for the preparation of these ocular inserts which comprises dissolving the water soluble polymer and if desired a plasticizer, buffering agent and/or preservative in a suitable solvent and the solution evaporated to afford a thin film of the polymer which can then be subdivided to prepare suitable inserts. Alternatively, the inserts can be prepared most conveniently using the thermoplastic properties of the polymer. For example, the polymer can be warmed at temperatures between 150° F. and 400° F. and then molded to form a thin film. It is generally preferred to prepare the inserts by molding or extrusion in accordance with procedures which are well known in the art.

The following examples are given by way of illustration.

EXAMPLE 1

Hydroxypropyl Cellulose Inserts

Cylindrical rod-shaped ophthalmic inserts are prepared by an injection molding procedure as described below:

The powdered hydroxypropyl cellulose (KLUCEL GF) is heated in a cup to 200° C. When the powder is melted and begins to flow, the valve at the outlet of the cup is opened and the molten mass is forced into a mold under the action of both pressure and the elastic melt extruder effect. The mold is then removed from the machine and opened. The specimen is removed from the mold and has a diameter of 1.25 mm. The specimen is cut into lengths of 10 mm. having a weight of about 12 mg. The ophthalmic inserts are plasticized by placing them into an 88% relative humidity cabinet for two days where they pick up 10–15% moisture.

Similar inserts are prepared having a diameter of 1.0 and 1.5 mm. and a length of 2, 4, 6, 10, 12, 15, 20 and 23 mm.

EXAMPLE 2

Hydroxypropyl Cellulose Inserts

Ophthalmic inserts are prepared by the compression molding procedure as described below:

Compression molded films are prepared on a Hydraulic Press by subjecting hydroxypropyl cellulose (KLUCEL HF) to a compressional force of 12,000 lbs. (gauge) at 300° F. for one to two minutes. The film is cooled under pressure by having cold water circulate in the platen. Film thickness is controlled by placing shims between the upper and lower compression plates holding the hydroxypropyl cellulose. Ophthalmic inserts are then individually cut from the film with a rectangular shaped punch, to afford individual inserts having a thickness of 0.55 mm., width of 2 mm., length of 12.5 mm. and a weight of about 12.5 mg.

EXAMPLE 3

Hydroxypropyl Cellulose Inserts

Ophthalmic inserts are prepared by a film casting procedure as described below:

A 1% (w/v) aqueous solution of hydroxypropyl cellulose (KLUCEL JF) is prepared and then poured onto a glass plate. The glass plate is then placed into a 50° C. hot air cabinet for 16 hours and the water is allowed to evaporate.

The resulting film is removed from the glass plate and ophthalmic inserts are then individually cut from the film with an oval shaped punch. The final insert has a diameter of 1.0 mm., length of 10 mm. and a weight of 7.0 mg.

EXAMPLE 4

Hydroxpropyl Cellulose Inserts

Cylindrical rod-shaped ophthalmic inserts are prepared by the extrusion procedure as described below:

The hydroxypropyl cellulose (KLUCEL HF) is fed into a screw extruder whose barrel is heated to 400° to 450° F. The hydroxypropyl cellulose is melted and then extruded through an orifice (0.04 inch to 0.065 inch). The extrudate while hot is then sized to form a monodiameter filament, which is then cut into 12 mm. lengths having a diameter of 1.0 mm. and a weight of 12.0 mg. The ophthalmic inserts are plasticized by placing them into an 88% relative humidity cabinet for two days where they pick up 10–15% moisture.

In a similar fashion, rod-shaped inserts are prepared having the following dimensions: length 12.0 mm., diameter 1.25 and 1.50 mm. and weight of about 15 and 21 mg., respectively.

EXAMPLE 5

Sodium alginate Inserts

Rectangle-shaped ophthalmic inserts are prepared by the film casting procedure as described below:

An aqueous solution of sodium alginate (high viscosity) is prepared and then poured onto a glass plate. The glass plate is then placed into a fifty degree celsius (50° C.) hot air cabinet for sixteen hours and the water is allowed to evaporate.

The resulting film is removed from the glass plate and ophthalmic inserts are then individually cut from the film with a rectangular shaped punch to afford rectangular inserts having a length of 2.5 millimeters, height of 0.55 millimeters, and an appropriate width to yield inserts which weigh about 2.5 milligrams.

In a similar fashion, rectangular shaped inserts are prepared having a length of 12.5 mm., a height of 0.55 mm. and width of 2.0 mm. and a weight of 14 mg.

EXAMPLE 6

Hydroxypropylmethyl Cellulose Inserts

Ophthalmic inserts are prepared by a film casting procedure as described below:

A 1% (W/v) aqueous solution of hydroxypropyl cellulose (Methocel 60) is prepared and then poured onto a glass plate. The glass plate is then placed into a 50° C. hot air cabinet for 16 hours and the water is allowed to evaporate.

The resulting film is removed from the glass plate and ophthalmic inserts are then individually cut from the film with a rectangular shaped punch to afford rectangular inserts having a length of 12.5 mm., height of 0.55 mm., width of 2 mm. and weight of 14 mg.

Methocel HG 60 is a commercial methyl cellulose product manufactured by the Dow Chemical Company and has a methoxyl percentage of 28–30%, a hydroxypropyl percentage of 7–12% is soluble in $H_2O$ and organic solvents, has a normal gel temperature of 60° F. and demonstrates an average viscosity of 50 centipoises (range 40–60, 2% aqueous solution).

EXAMPLE 7

Methyl Cellulose Inserts

Ophthalmic inserts are prepared by a film casting procedure as described below:

A 1% (w/v) aqueous solution of methyl cellulose (average molecular weight 75,000) is prepared and then poured onto a glass plate. The glass plate is then placed into a 50° C. hot air cabinet for 16 hours and the water is allowed to evaporate.

The resulting film is removed from the glass plate and ophthalmic inserts are then individually cut from the film with a rod-shaped punch. The insert has a diameter of 1 mm., a length of 8 mm. and weight of 6 mg.

EXAMPLE 8

Hydroxypropyl Cellulose 90%

Propylene Glycol 10%

Ophthalmic inserts are prepared by a film casting procedure as described below:

A 0.1% (w/v) aqueous solution of hydroxypropyl cellulose (KLUCEL HF) is prepared to contain 0.1% by weight propylene glycol and then poured onto a glass plate. The glass plate is then placed into a 50° C. hot air cabinet for 16 hours and the water is allowed to evaporate.

The resulting film is removed from the glass and ophthalmic inserts are then individually cut from the film with a round-shaped punch. The inserts have a diameter of 0.9 mm. and weight of 22 mg.

EXAMPLE 9

Hydroxypropyl Cellulose (HF) 90%

Glycerine 10%

Cylindrical rod-shaped ophthalmic inserts are prepared by an extrusion procedure as described below:

The hydroxypropyl cellulose/glycerine mixture is fed into a ¾" single screw extruder whose barrel is heated to 300°→350° F. The mixture is melted and then extruded through an orifice (0.04 inch to 0.065 inch). The extrudate while hot is then sized to form a monodiameter filament, which is then cut into lengths of 6 mm. having a diameter of 1.5 mm. and a weight of 11 mg.

EXAMPLE 10

Poly ethylene oxide Inserts

Ophthalmic inserts can be prepared by a film casting procedure as described below:

A 1% (w/v) aqueous solution of poly ethylene oxide having an average molecular weight of 1,000,000 is prepared and then poured onto a glass plate. The glass plate is then placed into a 50° C. hot air cabinet for 16 hours and the water is allowed to evaporate.

The resulting film is removed from the glass plate and ophthalmic inserts are then individually cut from the film with a rod-shaped punch. The insert has a diameter of 1 mm., a length of 6 mm. and a weight of 9 mg.

EXAMPLE 11

Benzalkonium Chloride 0.02%

Hydroxypropyl Cellulose 9.98

Ophthalmic inserts are prepared by a film casting procedure as described below:

A 1% (w/v) aqueous solution of hydroxypropyl cellulose (KLUCEL GF) is prepared to contain 0.02% by weight benzalkonium chloride and then poured onto a glass plate. The glass plate is then placed into a 50° C. hot air cabinet for 16 hours and the water is allowed to evaporate.

The resulting film is removed from the glass plate and ophthalmic inserts are then individually cut from the film with a rod-shaped punch. The diameter of the insert is 1.25 mm., length of 6 mm. and weight 7 mg. The ophthalmic inserts are plasticized by placing them into an 88% relative humidity cabinet for two days where they pick up 10–15% moisture.

EXAMPLE 12

Carboxypolymethylene Inserts

Ophthalmic inserts are prepared by a film casting procedure as described below:

A 1% (w/v) aqueous solution of carboxypolymethylene (average molecular weight 3 million) is prepared and then poured onto a glass plate. the glass plate is then placed into a 50° C. hot air cabinet for 16 hours and the water is allowed to evaporate.

The resulting film is removed from the glass plate and ophthalmic inserts are then individually cut from the film with a rectangular shaped punch. The insert has a length of 12.5 mm., a height of 0.7 mm., width of 2 mm. and weight of 18 mg. The ophthalmic inserts are plasticized by placing them into an 88% relative humidity cabinet for two days where they pick up 10–15% moisture.

EXAMPLE 13

Sodium Carbonate (anhydrous 0.25%

Hydroxypropyl Cellulose (KLUCEL GF) 9.75

Ophthalmic inserts can be prepared by a compression molding procedure as described below:

Compression molded films are prepared on a Carver Press by subjecting the hydroxypropyl cellulose/sodium carbonate (anhydrous) mixture to a compressional force of 12,000 lbs. (gauge) at 300° F. for one to two minutes. The film is cooled under pressure by having cold water circulate in the platen. Film thickness is controlled by placing shims between the upper and lower compression plates holding the hydroxypropyl cellulose. Ophthalmic inserts are then individually cut from the film with a rod-shaped punch. The insert has a diameter of 1.25 mm., a length of 10 mm. and weight of 12 mg. The ophthalmic inserts are plasticized by placing them into an 88% relative humidity cabinet for two days where they pick up 10–15% moisture.

With regard to the method of treatment aspect of this invention any water soluble non toxic polymer may be used including those on pages 3 and 4 as well as acrylic acid derivatives, PVA and polyvinyl pyrrolidine.

The inserts of this invention having length, breadth and thickness as well as failing to undergo any perceptible flow are necessarily solids, and contain as the sole therapeutically active agent one or more polymers selected from the aforementioned polymers.

It is highly preferred that the solid inserts of this invention are available for use by the patient in a pathogen free condition. Thus, it is preferred to sterilize the inserts and so as insure against recontamination, the sterilization is preferably conducted after packaging. The best mode of sterilizing is to employ ionizing irradiation including irradiation emanating from Cobalt 60 or high energy electron beams.

After packaging a convenient quantity of inserts, usually a single dose, the package is exposed to a sterilizing quantity of radiation. The preferred packaging employs sealing the inserts between layers of film or foil and then sealing or laminating the layers together about the edges. The techniques for performing the sterilization are well known and accepted, for example, as outlined in International Atomic Energy Commission, *Code of Practice for Radiosterilization of Medical Products*, 1967, pp. 423–431; and Block, *Disinfection, Sterilization and Preservation*, 2nd Ed., Lea & Febiger, Philadelphia, 1977, pp. 542–561.

The required quantity of irradiation can be determined experimentally by testing irradiated inserts for viable bacteria. Generally, the amount of irradiation desired to achieve sterilization is defined by the $D_{10}$ value. The $D_{10}$ value is the radiation dose that will reduce a given population of organisms by a factor of 10. Based on $D_{10}$ values, experimentally obtained for *Bacillus pumilus*, and presterilization contamination levels, a dose of 1.36 megarads is effective in obtaining a sterile product.

What is claimed is:

1. A solid sterile ophthalmic insert comprising as the sole therapeutically active agent a water soluble solid polymer; said insert having a dissolution time in lacrimal fluids of less than 24 hours and having a surface area of from about 5 to about 800 sq. mm., a length of from about 1–30 mm. and a width and height of from about 0.25 mm. to about 30 mm., said polymer being selected from the group consisting of a cellulose derivative, starch derivative, dextrose, polyalkylene glycol, polyvinylmethyl ether, polyethylene oxide, carboxyvinyl, and mixtures thereof.

2. The insert of claim 1 wherein the polymer is a cellulose derivative.

3. The insert of claim 2 wherein the polymer is a hydroxyloweralkyl cellulose, alkali carboxyloweralkyl cellulose, alkyl cellulose, and hydroxyloweralkyl-lower alkyl cellulose.

4. The insert of claim 3 wherein the polymer is hydroxypropyl cellulose.

5. The insert of claim 4 having a water content of between 1% and 40% by weight.

6. The insert of claim 1 wherein the surface area is from about 15–100 sq. mm. and the length is from about 5–20 mm. and the width and height is from about 1–5 mm.

7. The insert of claim 6 wherein the surface area is from about 5–50 sq. mm. and the length is from about 2–15 mm.

8. The insert of claim 5 wherein the water content is between 5% and 20% by weight.

9. A solid pathogen free ophthalmic insert comprising as the sole therapeutically active agent a water soluble solid polymer; said insert having a dissolution time in lacrimal fluids of less than 24 hours and having a surface area of from about 5 to about 800 sq. mm., a length of from about 1–30 mm. and a width and height of from about 0.25 mm. to about 30 mm., said polymer being selected from the group consisting of a cellulose derivative, starch derivative, dextrose, polyalkylene glycol, polyvinylmethyl ether, polyethylene oxide, carboxyvinyl, and mixtures thereof.

10. The insert of claim 9 wherein the polymer is hydroxypropyl cellulose.

11. The insert of claim 9 having between 1–40% by weight of water.

12. The insert of claim 9 wherein the water content is between 5–20%.

13. The insert of claim 9 wherein the polymer is hydroxyloweralkyl cellulose, alkali carboxyloweralkyl cellulose, alkyl cellulose, and hydroxyloweralkyl-lower alkyl cellulose.

14. A solid sterile ophthalmic insert in the form of a rod comprising as the sole therapeutically active agent a water soluble solid polymer; said insert having a dissolution time in lacrimal fluids of less than 24 hours and having a length of from about 2 to about 20 mm and a diameter of from about 0.5 to about 1.5 mm; said polymer being selected from the group consisting of a cellulose derivative, starch derivative, dextrose, polyalkylene glycol, polyvinylmethyl ether, polyethylene oxide, carboxyvinyl, and mixtures thereof.

15. The insert of claim 14 wherein said polymer is hydroxypropyl cellulose.

16. The insert of claim 14 wherein said plasticizer is water.

17. The insert of claim 14 wherein the water content is between 5–20%.

18. A method of treating keratoconjunctivitis sicca comprising administering to the eye of a keratoconjunctivitis sicca patient a solid sterile ophthalmic insert consisting essentially of a water soluble solid polymer, as the sole therapeutically active agent having a surface area of from about 5 to about 800 sq. mm., a length of from about 1–30 mm. and a width and height of from about 0.25 mm. to about 30 mm., said polymer being selected from the group consisting of a cellulose derivative, natural gum, starch derivative, dextrose, polyalkylene glycol, polyvinylmethyl ether, polyethylene oxide, carboxyvinyl, xanthan gum and mixtures thereof.

19. The method of claim 18 wherein the polymer is a cellulose derivative, alginate or pectin compound.

20. The method of claim 18 wherein the polymer is a hydroxyloweralkyl cellulose, alkali carboxyloweralkyl cellulose, alkyl cellulose, and hydroxyloweralkyl-lower alkyl cellulose.

21. The method of claim 18 wherein said polymer is hydroxypropyl cellulose.

22. The method of claim 18 wherein the insert has a surface area of from about 15–100 sq. mm., the length is from about 5–20 mm. and the width and height is from about 1–5 mm.

23. The method of claim 18 wherein the surface area of said insert is from about 5–50 sq. mm. and the length is from about 2–15 mm.

24. The method of claim 18 wherein said insert is in the form a rod.

25. The method of claim 18 wherein said insert is from about 1% to 40% by weight water.

26. The method of claim 18 wherein the insert is from 5% to 20% by weight water.

* * * * *